United States Patent [19]

Beijk et al.

[11] Patent Number: 4,777,444

[45] Date of Patent: Oct. 11, 1988

[54] METHOD AND APPARATUS FOR TESTING THE INTEGRITY OF AN ELECTRODE IN A POTENTIOMETRIC MEASURING ELECTRODE SYSTEM

[75] Inventors: Jozeph M. Beijk, Hooglanderveen; Teunis Both, Wilnis, both of Netherlands

[73] Assignee: Yokogawa Electric Corporation, Tokyo, Japan

[21] Appl. No.: 909,564

[22] Filed: Sep. 22, 1986

[30] Foreign Application Priority Data

Apr. 15, 1986 [EP] European Pat. Off. ........ 86200640.0

[51] Int. Cl.$^4$ ............................................. G01N 27/46
[52] U.S. Cl. ..................................... 324/439; 324/438; 324/514; 204/401; 204/420
[58] Field of Search ................ 204/401, 420; 324/438, 324/439, 514

[56] References Cited

U.S. PATENT DOCUMENTS

| | | | |
|---|---|---|---|
| 4,189,367 | 2/1980 | Connery et al. | 324/514 |
| 4,218,746 | 8/1980 | Koshiishi | 204/406 |
| 4,360,415 | 11/1982 | Brezinski | 204/406 |
| 4,430,164 | 2/1984 | Daroczy et al. | 204/401 |
| 4,680,537 | 7/1987 | Miller | 324/439 |
| 4,680,552 | 7/1987 | Shirato et al. | 324/439 |
| 4,686,011 | 1/1987 | Jäkle | 324/438 |

Primary Examiner—M. H. Paschall
Assistant Examiner—Jeffrey A. Gaffin
Attorney, Agent, or Firm—Moonray Kojima

[57] ABSTRACT

A testing method and apparatus for testing the condition of electrodes and their conductors in ion sensitive measuring or controlling systems, wherein the measuring circuit is disruptive and replaced by an impedance measuring circuit containing only one electrode, so that also failures of, for example, reference electrodes, soiling and deposits, and electrolyte loss, can be determined. The arrangement has sufficient accuracy to detect faults, defects and failures as they slowly come into existence.

5 Claims, 1 Drawing Sheet

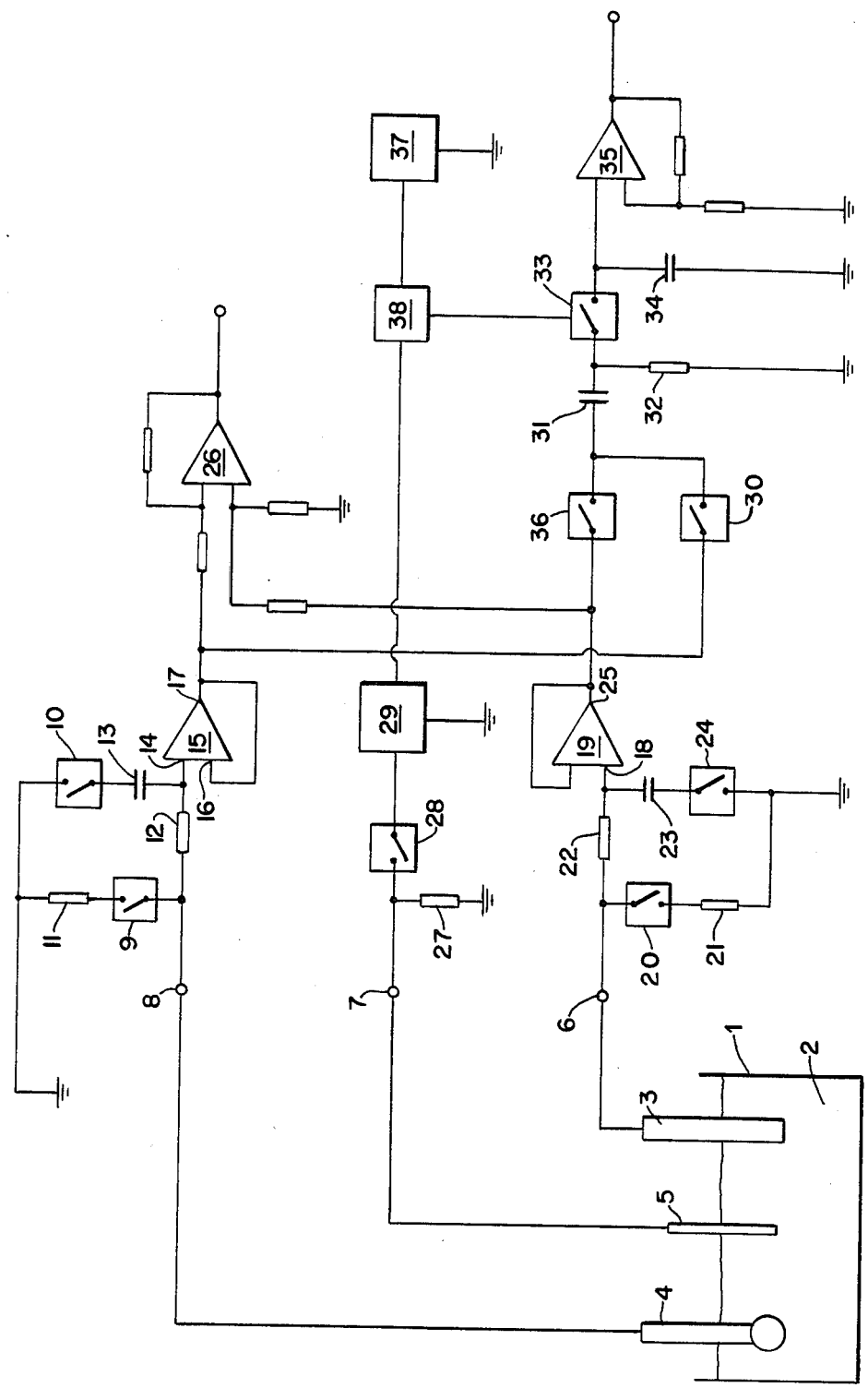

METHOD AND APPARATUS FOR TESTING THE INTEGRITY OF AN ELECTRODE IN A POTENTIOMETRIC MEASURING ELECTRODE SYSTEM

BACKGROUND OF THE INVENTION

1. Field of Invention

This invention relates to a method and apparatus for testing the integrity of an electrode in an electrode system for measuring an ion concentration or a redox potential in a solution, wherein in the circuit containing the electrode, a two directional electrical quantity is injected to determine the impedance of the electrode.

2. Discussion of the Prior Art

A conventional method and apparatus to carry out such testing is disclosed for example in U.S. Pat. No. 4,189,367 wherein the electrode system contains a high resistance ion selective membrane and a reference electrode. The impedance of the ion selective membrane is considerably greater than that of the reference electrode. For example, this may be by a factor 10 times greater than the combined impedance of the reference electrode and the solution. In practice, the impedance of the reference electrode is often about $10^{-3}$ to $10^{-5}$ times smaller than that of the high resistance ion selective electrode, which may be, for example, of glass.

In another example, U.S. Pat. No. 3,661,748 discloses a method and apparatus for testing the integrity of electrodes, wherein apart from electrodes for measuring concentrations of a gas, such as $O_2$ or $CO_2$ (which electrodes need a drving voltage and are not considered in this invention), a testing circuit is used for a series connection of a potentiometric electrode, such as a pH electrode, and a reference electrode. In this circuit, an AC voltage is injected in the series connection and phase-sensitive measuring is done of the AC current passing through the circuit. The AC voltage is applied to the system via an auxiliary electrode in contact with the liquid monitored by the ion sensitive electrode.

In both prior art disclosure, disadvantageously, the measuring circuit is maintained intact during the testing period. The result is that no individual testing of the ion sensitive electrode and the reference electrode is possible and that test values of each may be relatively inaccurate, whereas several types of failures may escape discovery, as may be apparent from the below discussion.

Apart from the high resistance membrane electrodes, such as glass electrodes, low impedance potentiometric electrodes exist, such as redox electrodes, which are selectively sensitive to for example Na, K or other ions.

When testing electrode systems, many types of electrode failures, faults and defects may occur. For example, apart from a short circuit originating from a crack in a glass electrode, for example, misreadings may be due to many other causes. Examples of other causes are:

(A) The connection with an electrode may be interrupted. In that case, its reading is highly constant, but may be in the region of normal readings.

(B) The electrode may be soiled or coated by deposits, so that its impedance increases and its sensitivity decreases, thus causing misreadings.

(C) The reference electrode may fail, due to loss of electrolyte, in which case its impedance will increase and its output may float, so that the value indicated by the electrode system will be false, but remain within the region of possible readings.

(D) The reference electrode is poisoned. For example, in case of a reference electrode of the type, metal-metal halide electrolyte, this may lead to a very strong increase of impedance, and even isolation of the electrode from the electrolyte, which will cause misreadings.

(E) The membrane of the reference electrode between its electrolyte and the liquid being monitored may become clogged, thus, leading to a high impedance of the reference electrode, which can even be put out of action.

In practice, failure to the reference electrode is a greater danger than the failure of, for example, the glass electrode. Furthermore, it is desired to be able to indicate not only the break down of a high impedance,but also other types of failures.

Thus, it can be appreciated that the prior art is replete with disadvantages and deficiencies.

SUMMARY OF THE INVENTION

Accordingly, an object of the invention is to overcome the aforementioned and other disadvantages and deficiencies of the prior art.

Another object is to provide a highly reliable method and apparatus for testing and monitoring electrodes in an electrode system.

A further object is to provide a monitoring method and apparatus, which are able to detect failure of each of the different electrodes of an electrode system for measuring ion concentration or a redox potential.

A still further object is to provide a method and apparatus which allow detection of impedances which are outside of a normal range, either being too high or too low.

The foregoing and other objects are attained by the invention which provides, in its broadest aspects, a method as indicated above, wherein the measuring circuit is replaced by test circuits, each containing only one of the electrodes of the system, and an auxiliary electrode, which test circuits each contain at least one impedance adapted to the impedance value of the one electrode of the system. Because the measuring circuit is not used during the test periods, the injected two dimensional electrical quantity cannot disturb the measurement, so that higher accuracy is obtained.

In several electrode systems for measuring ion concentration in a solution, a potential equalization electrode is present. such an electrode serves to clamp the electrical potential of the liquid to be measured at a predetermined voltage level, for example, to prevent the measuring electronics or instruments from receiving voltages outside their working range. Such an electrode may be of an inoxydizable metal, such as stainless steel. For normal measurements, it cannot replace the so-called reference electrode, which preferably contains a metal, a halide of that metal, and a halide electrolyte. For the purpose of the invention, the potential equalization electrode is, however, quite suitable, because any DC voltage component does not play any part whey carry out the method of the invention. Accordingly, a preferred embodiment provides that the auxiliary electrode be the potential equalization electrode.

In the known system of U.S. Pat. No. 4,189,367, the electrical quantity to be injected in the system is a current. This may result in difficulties in case of circuit interruption.

Accordingly, it is preferred to provide that the two dimensional electrical quantity be a square wave or a block voltage. A block voltage has the advantage that a very stable level is present for sampling. When sampling in the second half of the duration of one of the voltage levels, the sample value will be practically stable.

With the known method of the above U.S. Pat. No. 4,189,367, the temperature of the liquid is measured and the value of the electric current to be supplied to the electrode system is determined on the basis of the measured temperature. A temperature compensation is applied in the system because the impedance of the glass membrane is strongly dependent on the temperature and in fact doubles for temperatures increases of about 10° C.

When practicing the invention, an analoguous temperature compensation can be applied by varying the applied voltage or the circuit for measuring the current flowing as a result of this voltage. A further possibility is to measure the impedance of a monitored electrode and to compare the impedance with a value calculated on the basis of the liquid temperature.

The invention also encompasses an apparatus for testing the integrity of an electrode in an electrode system for measuring ion concentration or a redox potential in a solution, comprising terminals connected to a measuring electrode, a reference electrode and an auxiliary electrode, means for generating an electrical test quantity for feeding it to at least one of the terminals, switching means for forming a test circuit connected to the terminal of the auxiliary electrode and the terminal of a selected electrode of the measuring electrode system, first switching means for connecting the means for generating the electrical test quantity to one of the terminals, second switching means for connecting a balance impedance to the terminal of the one electrode of the measuring electrode system or that of the auxiliary electrode, and third switching means for connecting the terminal of the selected electrode to an output device.

Advantageously, the apparatus is suitable for successively testing the electrodes of an ion sensitive electrode system. A further advantage of such an apparatus is, that it is possible to switch in a measuring circuit adapted for the monitored impedance. In a practical case, a glass membrane is compared with a resistance which is considerably greater, for example, 5 times greater, than a resistance to be used for comparing with a reference electrode.

DETAILED DESCRIPTION OF PREFERRED EMBODIMENTS

The invention is further described with reference to the single FIGURE of the drawing, wherein a vessel 1 contains liquid 2, of which ion concentration, for example, the H ion concentration pH or the sodium ion concentration pNa is to be measured. This is done with an ion sensitive electrode system having a reference electrode 3 and an ion sensitive high impedance glass electrode 4. A potential equalization electrode 5 is also immersed in liquid 2. Electrodes 3,4 and 5 are connected to terminals 6,7,8 respectively, which serve as inputs of the measuring and testing systems of the invention.

MEASUREMENT MODE

During normal ion concentration measurements, switch 9 is open and switch 10 is closed. Consequently, a comparing resistor 11, having a value of, for example, 10M ohms, is out of circuit and a filter, formed by resistor 12 and capacitor 13, is active to remove disturbances picked up in the lead between electrode 4 and terminal 8. The smoothed voltage of terminal 8 is fed to the positive input 14 of an operational amplifier 15. Input 16 of amplifier 15 is connected to output 17. The operational amplifier 15 serves as an impedance match and its output voltage corresponds directly to the voltage of input 14.

In a corresponding manner, terminal 6 is connected to positive input 18 of operational amplifier 19, switch 20 being open, so that a comparing resistor 21, of, for example 2M ohms, is out of the circuit, whereas a disturbance is diverted by filter comprising resistor 22 and capacitor 23 being activated and switch 24 being closed.

The output 25 of operational amplifier 19 is connected to the positive inputof operational amplifier 26, the negative input of which is connected to the output 17 of amplifier 15. The output of amplifier 26 is used as a measuring terminal for measurement of ion concentration.

Terminal 7 of potential equalization electrode 5 is connected to earth by a relatively small resistor 27, of, for example, 10 k ohms. Switch 28 is open.

TEST MODE

When testing either of electrode 3 or 4, switch 28 is closed and a low impedance symmetrical block voltage generator 29 delivers a block voltage of, for example, 1 volt at 40 Hz to electrode 5 via terminal 7.

(TESTING ELECTRODE 4)

When testing electrode 4, switch 9 is closed, so that in the circuit,comprising earth, electrode 5, liquid 2, electrode 4, resistor 11, earth, the AC voltage of input 14 of amplifier 15 mainly depends on the impedance value of electrode 4 and liquid 2. An extremely high impedance points to rupture of connection or no liquid 2 between electrodes 4,5. An impedance which is higher than may be expected, but not as high as results from a rupture, points to soiling or coating of at least one of the electrodes 4,5 or an extemely low conductivity of the liquid 2. A low impedance points to a break down of electrode 4.

The output of amplifier 15 is fed to a capacitor 31, for example, of 2 F, through a switch 30, which is closed when testing electrode 4. Capacitor 31 is connected to earth via resistor 32 of, for example 10 k ohms.

A sampler switch 33 is adapted to close during a short period of the duration of one of the levels of the block voltage so that samples of this level are fed to a sample holding capacitor 34, connected to the positive input of an output operational amplifier 35. The voltage on the output of amplifier 35 is a measure for the impedance of electrode 4 and the liquid 2, independent of any failure of electrode 3. Further, this impedance can be measured even in the region of very high impedance pointing to rupture of leads.

Furthermore, filter circuit comprising resistor 12 and capacitor 13 is disrupted because of the opening of switch 10, so that it does not influence the measurement.

When testing electrode 4, switch 20 is open in order to prevent a shunt circuit via relatively small resistor 21 to earth. Switch 24 may be closed, whereas switch 36 is open, to prevent interference from electrode 3.

(TESTING ELECTRODE 3)

For testing reference electrode 3, switch 20 is closed and switch 24 is opened. Consequently, the filter circuit comprising resistor 22 and capacitor 23, is put out of action and resistor 21 is connected in series with the impedance of electrodes 5 and 3, and liquid 2 connecting them. At the same time, resistor 11 is switched off by opening switch 9 and the filter circuit comprising resistor 12 and capacitor 13 is activated by closing switch 10. Switch 28, for supplying the block voltage, is still closed, but the connection to blocking capacitor 31 is through switch 36, whereas switch 30 is opened. In the circuit comprising earth, electrode 5, liquid 2, reference electrode 3, resistor 21, earth, the impedance of reference electrode 3 is compared to that of resistor 21.

A high impedance value may be an indication of a lead rupture, soiling or coating of the outer membrane, loss of electrolyte or poisoning. A low impedance may point to some type of short circuit.

When testing electrodes 3, or 4, the output of amplifier 26 has no relevancy to any quantity to be measured and should be neglected.

Auxilliary electrode 5 is of a type which rarely breaks down. However, it is possible to become covered with an insulating deposit. In that case, an increase of the impedance measurement of electrode 3 will show up, which itself probably will have some additional resistance due to the deposit.

Because of the normally high resistance value of electrode 4, such a failure would be less clear in case only the impedance of that electrode is being measured. Moreover, a synchronous impedance increase of electrodes 3, and 4 could be an indication that something is wrong.

With the invention, monitoring of the temperature may be combined with adaption of the amplitude of the block voltage from generator 29, adaption of resistor 11, or simply, varying the region in which the impedance value has to be. Also, it is possible to use the invention with other electrodes, such as metal electrodes for redox measurements. Such electrodes have a low impedance value, but, in cases of soiling, coating, poisoning or rupture of connection, may show high impedances, thus always indicating any type of failure.

Although unnecessary, further switching means may be provided to switch off any electrode not incuded in any test circuit at the moment of testing.

In order to synchronize block voltage generator 29 with the sampling switch 33, a block voltage generator may provide a block voltage having ten times the frequency of generator 29. The generator 37 feeds a counter 38, which sends the first five out of each ten pulses toward generator 29 and the ninth and tenth pulses to switch 33.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. An apparatus testing the integrity of an electrode in a system for measuring ion concentration or redox potential in a solution, said apparatus comprising
   terminal connected to a measuring electrode, a reference electrode, and an auxiliary electrode;
   means for applying an electrical test quantity having two directions to at least one of said terminals;
   switching means for forming a test circuit connected to said terminal of said auxiliary electrode and to one of said terminals of said measuring electrode and said reference electrode;
   first switching means for connecting said means for applying the electrical test quantity to one of said terminals of said measuring electrode and said reference electrode;
   second switching means for connecting a balance impedance to one of said terminals of said measuring electrode and said reference electrode or to said terminal of said auxiliary electrode; and
   third switching means for connecting one of said terminals of said reference electrode and said measuring electrode to an output device; wherein
   said means for applying comprises means for generating a block voltage having equal positive and negative levels of predetermined duration; and wherein
   said output device comprises a blocking capacitor and a sampling and holding circuit, wherein sampling by said sampling and holding circuit is carried out in a second half of said duration of occurrence of one of said levels.

2. The method of claim 1, wherein said auxiliary electrode is a potential equalization electrode, said auxiliary electrode being separate from said reference and measuring electrodes, wherein said two directional electrical quantity is a block voltage, wherein said auxiliary electrode and one electrode of said reference and measuring electrodes receives said block voltage and said one electrode is connected in a voltage divider circuit containing an impedance, the output of said divider circuit being fed to a blocking capacitor, the output of which provides a signal related to impedance of the electrode to be tested, and wherein said signal is subjected to a sampling and holding process, which is synchronous with said block voltage, said block voltage having different levels of predetemined duration, said sampling occuring in the second half of the duration of one of said levels of said block voltage.

3. The method of claim 2, wherein the two directional electrical quantity is a square wave voltage.

4. Method of claim 2, wherein a plurality of test circuits is formed one after another, each containing said auxiliary electrode and one electrode of said electrode system being tested.

5. A method testing the integrity of an electrode in a potentiometric measuring system for measuring concentration or redox potential, said system comprising a reference electrode, a measuring electrode, both said reference electrode and said measuring electrode being immersed in liquid, and a measuring circuit for measuring DC potential difference between said reference electrode and said measuring electrode, and using an auxiliary electrode and a separate fault test circuit means, said method comprising the steps of
   generating a two directional electrical quantity;
   connecting alternately said reference electrode and said measuring electrode to said separate fault test circuit means;
   applying said two directional electrical quantity to said auxiliary electrode, said auxiliary electrode being immersed in said liquid when testing said reference electrode or said measuring electrode; and
   measuring, by use of said separate fault test circuit means, the impedance value between said auxiliary electrode and said reference electrode, and the impedance value between said auxiliary electrode and said measuring electrode in response to applying said two directional electrical quantity so that failure of said reference electrode or said measuring electrode is determined on basis of said impedance value with the output of said measuring circuit being neglected during the test period.

* * * * *